(12) United States Patent
Urnezis et al.

(10) Patent No.: US 6,350,480 B1
(45) Date of Patent: Feb. 26, 2002

(54) CHEWING GUM PRODUCT INCLUDING A HYDROPHILIC GUM BASE AND METHOD OF PRODUCING

(75) Inventors: Philip W. Urnezis, Lombard, IL (US); Philip Mazzone, Griffith, IN (US); Michael J. Greenberg, Northbrook, IL (US); Michael T. Bunczek, Lisle, IL (US); David G. Barkalow, Deerfield, IL (US); George W. Monen, Woodridge, IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/749,983

(22) Filed: Dec. 27, 2000

Related U.S. Application Data

(60) Provisional application No. 60/173,736, filed on Dec. 30, 1999.

(51) Int. Cl.$^7$ .............................. A23G 3/30; A61K 9/68
(52) U.S. Cl. ............................. 426/5; 424/48; 424/440; 426/3; 426/6
(58) Field of Search ....................... 426/3, 5, 6; 424/48, 424/440

(56) References Cited

U.S. PATENT DOCUMENTS

| | | | | |
|---|---|---|---|---|
| 2,990,328 A | * | 6/1961 | Lincoln | |
| 4,238,510 A | * | 12/1980 | Cherukuri et al. | 426/5 |
| 4,317,838 A | * | 3/1982 | Cherukuri et al. | 426/5 |
| 4,374,858 A | * | 2/1983 | Glass et al. | 426/5 |
| 4,378,374 A | | 3/1983 | Reggio et al. | 426/3 |
| 4,386,106 A | * | 5/1983 | Merritt et al. | 426/5 |
| 5,110,608 A | | 5/1992 | Cherukuri et al. | 426/3 |
| 5,433,960 A | * | 7/1995 | Meyers | 426/5 |
| 5,569,477 A | * | 10/1996 | Nesbitt | 426/5 |
| 5,601,858 A | | 2/1997 | Mansukhani et al. | 426/3 |
| 5,846,557 A | | 12/1998 | Eisenstadt et al. | 424/439 |
| 5,858,383 A | | 1/1999 | Precopio | 424/405 |
| 5,858,412 A | | 1/1999 | Staniforth et al. | 424/489 |
| 5,858,413 A | | 1/1999 | Jettka et al. | 424/682 |
| 5,858,423 A | | 1/1999 | Yajima et al. | 426/3 |
| 5,866,179 A | | 2/1999 | Testa | 426/3 |
| 5,889,028 A | | 3/1999 | Sandborn et al. | 514/343 |

FOREIGN PATENT DOCUMENTS

| WO | 98/23165 | * | 6/1998 | 426/5 |
|---|---|---|---|---|

* cited by examiner

*Primary Examiner*—Arthur L. Corbin
(74) *Attorney, Agent, or Firm*—Steven P. Shurtz; Brinks Hofer Gilson & Lione

(57) ABSTRACT

A method for producing a chewing gum with an improved release of a lipophilic active agent, as well as the chewing gum so produced, is obtained by using a hydrophilic gum base. The preferred and novel gum base includes hydrophilic polymers, hydrophilic softeners/emulsifiers and fillers, but is essentially free of hydrophobic elastomers and hydrophobic softeners, as well as waxes and elastomer solvents. The lipophilic active agent is preferably added to a coating on a chewing gum pellet made using a hydrophilic gum base, such as by being mixed into a coating solution. The coating solution may contain a high-intensity sweetener. An active agent may also be used in the gum core.

30 Claims, No Drawings

CHEWING GUM PRODUCT INCLUDING A HYDROPHILIC GUM BASE AND METHOD OF PRODUCING

REFERENCE TO EARLIER FILED APPLICATION

The present application claims the benefit of the filing date under 35 U.S.C. §119(e) of provisional U.S. Patent Application, Ser. No. 60/173,736, filed Dec. 30, 1999, which is hereby incorporated by reference.

BACKGROUND OF THE INVENTION

The present invention relates to methods for producing chewing gum. More particularly, the invention relates to producing chewing gum containing an effective amount of an active medicament. Preferably, the active medicament is added to the chewing gum coating to improve its rate of release from chewing gum and improve its release by using a hydrophilic base composition.

In recent years, efforts have been devoted to controlling release characteristics of various ingredients in chewing gum. Most notably, attempts have been made to delay the release of sweeteners and flavors in various chewing gum formulations to thereby lengthen the satisfactory chewing time of the gum. Delaying the release of sweeteners and flavors can also avoid an undesirable overpowering burst of sweetness or flavor during the initial chewing period. On the other hand, some ingredients have been treated so as to increase their rate of release in chewing gum.

Besides sweeteners, other ingredients may require a controlled release from chewing gum. In certain embodiments, it is contemplated that a lipophilic active medicament that is added to the gum coating is generally released very readily. An active may be added to the gum coating, which is a water soluble matrix, such that, during the chewing period, the active agent may be released quickly, resulting in a fast release. This would allow a chewing gum coating to be a carrier for an active medicament with these fast release characteristics. However, during chewing the lipophilic active agent may become bound to the chewing gum base composition, and not released in sufficient quantity for effectiveness.

It is of course known to provide active medicaments to individuals for various purposes. These medicaments can be used to treat diseases and as such are typically referred to as drugs or medicaments. Likewise, the drugs or medicaments can be used for preventive purposes. Still, it is known to provide medicaments to an individual for a variety of non-medical purposes including enhancing performance or maintaining health.

There are a great variety of such medicaments. These medicaments run the gamut from stimulants such as caffeine to drugs such as analgesics, tranquilizers, cardiovascular products, as well as vitamins, and supplements. Some such medicaments are taken on an "as-needed" basis while other medicaments must be taken at regular intervals by the individual.

There is therefore a need for an improved method of delivering lipophilic active agents to an individual.

SUMMARY OF THE INVENTION

The present invention provides improved methods for delivering a medicament or active agent to an individual. To this end, coated chewing gum products are provided including a medicament or active agent. The medicament or active agent is present within the coating of a chewing gum composition. It has been found that by adding the active agent to a gum coating, the medicament or active agent is quickly released from the chewing gum into saliva. Continuing to chew the chewing gum may create a pressure within the buccal cavity and may force the medicament or active agent or medicament directly into the systemic system of the individual through the oral mucosa contained in the oral cavity. However, the lipophilic active agent may become partially bound in the chewing gum base and gum matrix and not be completely released.

In one aspect, the present invention is a hydrophilic gum base comprising:
   a) about 20% to about 90% hydrophilic polymers;
   b) about 5% to about 35% hydrophilic softeners/emulsifiers; and
   c) about 4% to about 50% filler;
   d) the chewing gum base being essentially free of hydrophobic polymers, elastomer solvents, waxes and hydrophobic softeners.

Improved chewing gum products including medicaments and active agents in a gum coating and a hydrophilic base composition are also provided by the present invention.

To this end, the present invention provides a method of drug delivery comprising the steps of: providing a hydrophilic chewing gum core and a chewing gum coating that includes a medicament in the chewing gum coating; and chewing the chewing gum to cause the medicament to be released from the chewing gum coating into the oral cavity of the chewer.

The active medicament may be any agent that is lipophilic and is traditionally used as a medicament and lends itself to being administered through the oral cavity. Such active agents may be vitamins, cancer chemotherapeutics; antimycotics; oral contraceptives, analgesics, antacids, muscle relaxants, antihistamines, decongestants, antibacterial agents, anesthetics, antitussives, diuretics, anti-inflammatories, antibiotics, AIDS medication, neurological drugs, antivirals, psychotherapeutic agents, anti-diabetic agents, cardiovascular agents, nutraceuticals and nutritional supplements.

Accordingly, an advantage of an embodiment of the present invention is to provide new methods for delivering lipophilic medicaments or active agents to an individual.

Further, an advantage of an embodiment of the present invention is to provide a method of administering a lipophilic medicament or agent to an individual at a lower level than is typically administered orally while still achieving the same effect.

Additionally, an advantage of an embodiment of the present invention is to provide a method of administering lipophilic drugs that is more palatable than current methods.

Moreover, an advantage of an embodiment of the present invention is to provide an improved method for drug delivery.

DETAILED DESCRIPTION OF THE PREFERRED EMBODIMENTS

The present invention provides improved methods for delivering medicaments and other active agents to an individual, as well as improved gum base and chewing gum formulations. As used herein, the term chewing gum also includes bubble gum and the like. Pursuant to the present invention, a medicament or active agent is contained in the coating of a chewing gum formulation, in contrast to some prior such formulations where the medicament or active agent is contained directly in the chewing gum composition.

Accordingly, as the chewing gum is chewed, the active agent is released into the saliva more quickly. During continual chewing, the medicament or active in the saliva may be then forced due to the pressure created by the chewing gum through the oral mucosa in the oral cavity.

When an active such as vitamin E is added to a gum coating, the active agent will have an increased water dispersability, and release quickly into the mouth from the gum coating. Depending on the active agent, which will generally be non-water soluble but oil soluble or lipophilic, adding the active agent to a gum coating will increase the release of the active agent from chewing gum.

Other agents or medicaments may be included in the present invention. By the term "active agent" the present invention refers to a compound that has a desired therapeutic or physiological effect once ingested and/or metabolized. The therapeutic effect may be one which decreases the growth of a xenobiotic or other gut flora or fauna, provides the physical relief from a malady (e.g., diminishes pain, acid reflux or other discomfort), has an effect on the brain chemistry or molecules that determine mood and behavior, or has improved nutritional benefits. Of course these are just examples of what is intended by therapeutic effect. Those of skill in the art will readily recognize that a particular agent has or is associated with a given therapeutic effect.

The active agent may be any agent that is traditionally used as a medicament and lends itself to being administered through the oral cavity. Such active agents may be vitamins, cancer chemotherapeutics, antimycotics, oral contraceptives, analgesics, antacids, muscle relaxants, antihistamines, decongestants, anesthetics, antitussives, diuretics, anti-inflammatories, antibiotics, antivirals, psychotherapeutic agents, anti-diabetic agents, cardiovascular agents, bioengineered pharmaceuticals, nutraceuticals and nutritional supplements. Vitamins particularly that may be delivered using this invention include, and are mostly limited to, fat soluble vitamins such as thiamin, riboflavin, pyridoxine, pantothenic acid, choline, carnitine, vitamin D and its analogs, vitamin A and the carotenoids, retinoic acid, vitamin E and vitamin K.

Compositions that may be formulated into a suitable chewing gum formulation are described in, for examples, U.S. Pat. Nos. 5,858,423; 5,858,413; 5,858,412 and 5,858,383. Additionally, Goodman and Gilman's "The Pharmaceutical Basis of Therapeutics" (Eds. Hardman et al., Publ. McGraw Hill, N.Y.) provides comprehensive guidance of useful drugs and their mechanisms of action. Medicated chewing gums have been particularly effective in the delivery of agents such as nicotine as described in, for example, U.S. Pat. Nos. 5,866,179; and 5,889,028. U.S. Pat. No. 5,846,557 describes general chewing gum compositions containing cough suppressing agents. These patents are incorporated herein by reference as providing a teaching of the incorporation of medicinal agents into oral chewable formulations. It should be understood that the present chewing gum formulation(s) and coatings are not limited to the agents listed herein above, indeed any lipophilic medicinal or other active agent that lends itself to ingestion may be formulated into the chewing gum coatings and used in the present invention.

Nutraceuticals and nutritional supplements may also be added to chewing gums as well as the gum coatings as active agents. Among these are lipophilic herbs and botanicals that include, but are not limited to capsicum, chamomile, cat's claw, echinacea, garlic, ginger, ginko, various ginseng, green tea, golden seal, kava kava, nettle, passion flower, saw palmetto, St. John's wort, and valerian. Other nutraceuticals that also can be added to chewing gum coating as active agents are benzoin, glucosamine, grapeseed extract, guarana, phosphotidylserine, phytosterols, phytochemicals, isoflavones, lecithin, lycopene and polyphenol as well as weight loss agents such as phenylpropanolamine.

The level of medicament or agent in the chewing gum formulation and in the coating is selected so as to create, when the gum is chewed, a sufficiently high concentration of the medicament or agent in the saliva.

Pursuant to the present invention, depending on the agent or medicament, the dosing regiment will change. For example, if the medicament is an analgesic, the chewing gum product would be taken on an "as-needed" basis. Of course, similar to the oral administration of an analgesic, there would be restrictions on the number of pieces of chewing gum product chewed, for example, not more often than one pellet every four hours and not more often than four to five times a day. If the agent is a vitamin such as vitamin E to be used to enhance performance or other nutritional benefit, then the chewing gum product would be chewed as needed.

Referring now to the chewing gum, pursuant to the present invention the chewing gum may be based on a variety of different chewing gums that are known. For example, the chewing gums can be low or high moisture, sugar or sugarless, low calorie (via high base or low calorie bulking agents), and/or may contain dental agents.

Lipophilic active agents may be added to the gum coating along with sweeteners, more specifically high-intensity sweeteners such as thaumatin, dihydrochalcones, acesulfame K, aspartame, N-substituted APM derivatives such as neotame, sucralose, alitame, saccharin and cyclamates. These can also have the effect of reducing unpleasant tastes such as bitterness. Additional bitterness inhibitors or taste maskers can also be combined with active agents and sweeteners to give a reduced unpleasant taste.

Lipophilic active agents may also be combined in a coated chewing gum product. Multiple actives, such as vitamins, may be added to a gum coating for fast release but not added to the gum center unless encapsulated for later release. If the active agent has an affinity for the gum base, it may naturally give a slow release without encapsulation. If the active agent normally has a fast release, it would have to be encapsulated or entrapped for the desired time release.

In many instances, active medicaments may have a low quality off-taste or bitterness if added to a chewing gum coating. In most cases, this off taste may be masked with high intensity sweeteners, but in other instances, a bitterness inhibitor may be needed to reduce a bitter taste of a medicament.

There are a wide variety of bitterness inhibitors that can be used in food products as well as with active agents. Some of the preferred bitterness inhibitors are the sodium salts which are discussed in the article *Suppression of Bitterness by Sodium: Variations Among Bitter Taste Stimuli,* by R. A. S. Breslin and G. K. Beceuchenp from Monell Chemical Senses Center, Philadelphia, Pa. Sodium salts discussed are sodium acetate and sodium gluconate. Other sodium salts that may also be effective are sodium glycinate, sodium ascorbate and sodium glycerolphosphate. Among these, the most preferred is sodium gluconate and sodium glycinate, since they have a low salty taste and are most effective to reduce bitterness of most active medicaments.

Most of the sodium salts are very water soluble and are readily released from chewing gum coating to function as bitterness inhibitors. In most instances, the sodium salts which release readily from a chewing gum center may be modified by encapsulation to give an even faster release from chewing gum. However, in some instances the sodium salts would be encapsulated or entrapped to give a delayed release from gum. Generally, the bitterness inhibitor should release with the active medicament for maximum effectiveness.

Release of the medicament from gum coating may also be effected by particle size of the medicament. Small particles release more quickly whereas large particles release more slowly. Fast release can also be accomplished by dissolving the medicament in a liquid used to make a gum coating.

In general, a chewing gum composition typically comprises a water-soluble bulk portion, a water-insoluble chewable gum base portion and typically water-insoluble flavoring agents. The water-soluble portion dissipates with a portion of the flavoring agent over a period of time during chewing. The gum base portion is retained in the mouth throughout the chew.

The unique insoluble gum base of the present invention will comprise hydrophilic polymers (also referred to as polar polymers), including various molecular weights of polyvinyl acetate, short and medium chain polyesters or polyamides, and short and medium side chain poly (vinyl esters) (e.g. polyvinyl butyrates, polyvinyl propionates). The insoluble gum base will be essentially free of hydrophopic polymers such as natural and synthetic rubber elastomers, particularly butyl elastomers, polyisobutylene and styrene butadiene rubber elastomers. The insoluble gum base will also be essentially free of elastomer solvents, such as terpene resins, ester gums and rosin esters. The insoluble gum base will contain hydrophilic softeners/emulsifiers, but will be essentially free of hydrophobic softeners. The insoluble gum base can constitute about 5% to about 95% by weight of the chewing gum, more commonly about 10% to about 50% of the gum or about 25% to 35% by weight of the gum.

In a particular embodiment, the chewing gum base of the present invention contains about 20% to about 90% by weight hydrophilic polymers, about 4% to about 50% by weight filler, about 5% to about 35% by weight hydrophilic softeners/emulsifiers, and optional minor amounts (about 1% or less by weight) of miscellaneous ingredients such as colorants, antioxidants, etc.

Fillers/texturizers may include magnesium and calcium carbonate, ground limestone, silicate types such as magnesium and aluminum silicate, clay, alumina, talc, titanium oxide, mono-, di- and tri-calcium phosphate, cellulose polymers, such as oat fiber, and combinations thereof.

Hydrophilic softeners/emulsifiers may include glycerol monostearate, glycerol triacetate, lecithin, mono-, and diglycerides, and short and medium chain triglycerides, acetylated monoglycerides, and combinations thereof.

Colorants and whiteners may include FD&C-type dyes and lakes, fruit and vegetable extracts, titanium dioxide, and combinations thereof.

In addition to a water insoluble gum base portion, a typical chewing gum composition includes a water soluble bulk portion and one or more flavoring agents. The water soluble portion can include bulk sweeteners, high intensity sweeteners, flavoring agents, softeners, emulsifiers, colors, acidulants, fillers, antioxidants, and other components that provide desired attributes.

Softeners are added to the chewing gum in order to optimize the chewability and mouth feel of the gum. The softeners, which are also known as plasticizers and plasticizing agents, generally constitute between approximately 0.5% to about 15% by weight of the chewing gum. The softeners may include glycerin, lecithin, and combinations thereof. Aqueous sweetener solutions such as those containing sorbitol, hydrogenated starch hydrolysates, corn syrup and combinations thereof, may also be used as softeners and binding agents in chewing gum.

Bulk sweeteners include both sugar and sugarless components. Bulk sweeteners typically constitute about 5% to about 95% by weight of the chewing gum, more typically, about 20% to about 80% by weight, and more commonly, about 30% to about 60% by weight of the gum. Sugar sweeteners generally include saccharide-containing components commonly known in the chewing gum art, including but not limited to, sucrose, dextrose, maltose, dextrin, dried invert sugar, fructose, levulose, glactose, corn syrup solids, and the like, alone or in combination. Sugarless sweeteners include, but are not limited to, sugar alcohols such as sorbitol, mannitol, xylitol, hydrogenated starch hydrolysates, maltitol, and the like, alone or in combination.

High intensity artificial sweeteners can also be used, alone or in combination, with the above. Preferred sweeteners include, but are not limited to, sucralose, aspartame, N-substituted APM derivatives such as neotame, salts of acesulfame, alitame, saccharin and its salts, cyclamic acid and its salts, glycyrrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extrusion may be used to achieve the desired release characteristics.

Combinations of sugar and/or sugarless sweeteners may be used in chewing gum. Additionally, the softener may also provide additional sweetness such as with aqueous sugar or alditol solutions.

If a low calorie gum is desired, a low caloric bulking agent can be used. Examples of low caloric bulking agents include: polydextrose; Raftilose, Raftilin; fructooligosaccharides (NutraFlora); palatinose oligosaccharide; guar gum hydrolysate (Sun Fiber); or indigestible dextrin (Fibersol). However, other low calorie bulking agents can be used.

A variety of flavoring agents can also be used, if desired. The flavor can be used in amounts of about 0.1 to about 15 weight percent of the gum, and preferably, about 0.2% to about 5% by weight. Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

In general, chewing gum is manufactured by sequentially adding the various chewing gum ingredients to a commercially available mixer known in the art. After the ingredients have been thoroughly mixed, the gum mass is discharged from the mixer and shaped into the desired form, such as rolling into sheets and cutting into sticks, extruding into chunks or casting into pellets, which are then coated or panned.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further parts of the bulking agent are added to the mixer. Flavoring agents are typically added with the final portion of the bulking agent. Other optional ingredients are added to the batch in a typical fashion, well known to those of ordinary skill in the art.

The entire mixing procedure typically takes from five to fifteen minutes, but longer mixing times may sometimes be required. Those skilled in the art will recognize that many variations of the above described procedure may be followed.

In this invention, lipophilic medicaments or actives are used in the coating/panning of a pellet chewing gum. Pellet or ball gum is prepared as conventional chewing gum but formed into pellets that are pillow shaped, or into balls. The pellets/balls can then be sugar coated or panned by conventional panning techniques to make a unique coated pellet gum. The lipophilic active agent will be soluble in flavor or can be blended with other powders often used in some types of conventional panning procedures. Lipophilic active agents are isolated from other gum ingredients, which modifies their release rate from chewing gum. Levels of actives may be about 10 ppm to 30% by weight of chewing gum coating. The weight of the coating may be about 20% to about 50% of the weight of the finished product, but may be as much as 75% of the total gum product. The active agent will generally be used at a level of about 12 micrograms to about 250 milligrams per gram of coated chewing gum product. The active level will generally be based on the dosage for one or two pellets.

Conventional panning procedures generally coat with sucrose, but recent advances in panning have allowed other carbohydrate materials to be used in place of sucrose. Some of these components include, but are not limited to, dextrose, maltose, palatinose, xylitol, lactitol, hydrogenated isomaltulose, erythritol, maltitol, and other new alditols or combinations thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetables gums like alginates, locust bean gum, guar gum, and gum tragacanth, insoluble carbonates like calcium carbonate or magnesium carbonate and talc. Antitack agents may also be added as panning modifiers, which allow the use of a variety of carbohydrates and sugar alcohols to be used in the development of new panned or coated gum products. Flavors may also be added with the sugar or sugarless coating and with the active to yield unique product characteristics.

Another type of pan coating could also isolate the lipophilic active agent from the chewing gum ingredients. This technique is referred to as a film coating and is more common for pharmaceuticals than in chewing gum, but procedures are similar. A film like shellac, zein, or cellulose type material is applied onto a pellet-type product forming a thin film on the surface of the product. The film is applied by mixing the polymer, plasticizer and a solvent (pigments are optional) and spraying the mixture onto the pellet surface. This is done in conventional type panning equipment, or in more advanced side-vended coating pans. Since lipophilic active agents will be alcohol soluble, they may be readily added with this type of film. When a solvent like an alcohol is used, extra precautions are needed to prevent fires and explosions, and specialized equipment must be used.

Some film polymers can use water as the solvent in film coating. Recent advances in polymer research and in film coating technology eliminates the problem associated with the use of solvents in coating. These advances make it possible to apply aqueous films to a pellet or chewing gum product. Some lipophilic active agents can be suspended in this aqueous film or even an alcohol solvent film, in which an active agent is highly soluble. This film may also contain a flavor along with a polymer and plasticizer. The active agent can also be suspended in the aqueous or non-aqueous solvent and coated on the surface with the aqueous film. In some instances a combination of film and sugar or polyol coating may be useful, especially if the active agent is added with the film coating material. Also the film coating may be applied early, middle, or late in the coating process. This will give a unique release of active agent from a film-coated product.

After a coating film with a lipophilic active medicament is applied to a chewing gum product, a hard shell sugar or polyol coating may then be applied over the film coated product. In some instances a soft shell sugar or polyol coating may also be used over the film coated product. The level of film coating applied to a pellet gum may be generally from about 0.5% to about 3% of the gum product. The level of overcoating of the hard or soft shell may be about 20% to about 75%. When the active agent is added with the film coating and not with the sugar/polyol coating, better control of the amount of active agent in the product may be obtained. In addition, the sugar/polyol overcoating may give an improved stability to the active agent in the product.

As noted above, the coating may contain ingredients such as flavoring agents, as well as artificial sweeteners and dispersing agents, coloring agents, film formers and binding agents. Flavoring agents contemplated by the present invention include those commonly known in the art such as essential oils, synthetic flavors or mixtures thereof, including but not limited to oils derived from plants and fruits such as citrus oils, fruit essences, peppermint oil, spearmint oil, other mint oils, clove oil, oil of wintergreen, anise and the like. The flavoring agents may be used in an amount such that the coating will contain from about 0.2% to about 3% flavoring agent, and preferably from about 0.7% to about 2.0% flavoring agent. Active agents may be preblended with the flavor used in the coating.

Artificial sweeteners contemplated for use in the coating include but are not limited to synthetic substances, saccharin, thaumatin, alitame, saccharin salts, aspartame, N-substituted APM derivatives such as neotame, sucralose and acesulfame-K. The artificial sweetener may be added to the coating syrup in an amount such that the coating will contain from about 0.01% to about 0.5%, and preferably from about 0.1% to about 0.3% artificial sweetener.

Dispersing agents are often added to syrup coatings for the purpose of whitening and tack reduction. Dispersing agents contemplated by the present invention to be employed in the coating syrup include titanium dioxide, talc, or any other antistick compound. Titanium dioxide is a presently preferred dispersing agent of the present invention. The dispersing agent may be added to the coating syrup in amounts such that the coating will contain from about 0.1% to about 1%, and preferably from about 0.3% to about 0.6% of the agent.

Coloring agents are preferably added directly to the syrup in a dye or lake form. Coloring agents contemplated by the present invention include food quality dyes. Film formers preferably added to the syrup include methyl cellulose, gelatins, hydroxypropyl cellulose, ethyl cellulose, hydroxyethyl cellulose, carboxymethyl cellulose and the like and combinations thereof. Binding agents may be added either as an initial coating on the chewing gum center or may be added directly into the syrup. Binding agents contemplated by the present invention include gum arabic, gum talha (another type of acacia), alginate, cellulosics, vegetable gums and the like.

The coating is initially present as a liquid syrup which contains from about 30% to about 80% or 85% of the coating ingredients previously described herein, and from about 15% or 20% to about 70% of a solvent such as water. In general, the coating process is carried out in a rotating pan. Sugar or sugarless gum center tablets to be coated are placed into the rotating pan to form a moving mass.

The material or syrup which will eventually form the coating is applied or distributed over the gum center tablets. Flavoring agents may be added before, during and after applying the syrup to the gum centers. Once the coating has dried to form a hard surface, additional syrup additions can be made to produce a plurality of coatings or multiple layers of hard coating.

In a hard coating panning procedure, syrup is added to the gum center tablets at a temperature range of from about 100° F. to about 240° F. Mostly, the syrup temperature is from about 130° F. to about 200° F. throughout the process in order to prevent the polyol or sugar in the syrup from crystallizing. The syrup may be mixed with, sprayed upon, poured over, or added to the gum center tablets in any way known to those skilled in the art.

In general, a plurality of layers is obtained by applying single coats, allowing the layers to dry, and then repeating the process. The amount of solids added by each coating step depends chiefly on the concentration of the coating syrup. Any number of coats may be applied to the gum center tablet. Generally, no more than about 75–100 coats are applied to the gum center tablets. The present invention contemplates applying an amount of syrup sufficient to yield a coated comestible containing about 10% to about 75% coating. Where higher dosage of an active agent is needed, the final product may be higher than 75% coating.

Those skilled in the art will recognize that in order to obtain a plurality of coated layers, a plurality of premeasured aliquots of coating syrup may be applied to the gum center tablets. It is contemplated, however, that the volume of aliquots of syrup applied to the gum center tablets may vary throughout the coating procedure.

Once a coating of syrup is applied to the gum center tablets, the present invention contemplates drying the wet syrup in an inert medium. A preferred drying medium comprises air. Forced drying air contacts the wet syrup coating in a temperature range of from about 70° to about 115° F. Generally, the drying air is in the temperature range of from about 80° to about 100° F. The invention also contemplates that the drying air possess a relative humidity of less than about 15 percent. Preferably, the relative humidity of the drying air is less than about 8 percent.

The drying air may be passed over and admixed with the syrup coated gum centers in any way commonly known in the art. Generally, the drying air is blown over and around or through the bed of the syrup coated gum centers at a flow rate, for large scale operations, of about 2800 cubic feet per minute. If lower quantities of material are being processed, or if smaller equipment is used, lower flow rates would be used.

For many years, flavors have been added to a sugar coating of pellet gum to enhance the overall flavor of the gum. These flavors include spearmint flavor, peppermint flavor, wintergreen flavor, and fruit flavors. These flavors are generally preblended with the coating syrup just prior to applying it to the core, or added together with the syrup in one or more coating applications in a revolving pan containing the cores. Generally, the coating syrup is very hot, about 130° to 200° F., and the flavor may volatilize if preblended with the coating syrup too early.

The concentrated coating syrup is applied to the gum cores as a hot liquid, the sugar or polyol allowed to crystallize, and the coating then dried with warm, dry air. This is repeated in about 30 to 100 applications to obtain a hard shell coated product having an increased weight gain of about 40% to 75%. A flavor is applied with one, two, three or even four or more of these coating applications. Each time flavor is added, several non-flavored coatings are applied to cover the flavor before the next flavor coat is applied. This reduces volatilization of the flavor during the coating process.

For mint flavors such spearmint, peppermint and wintergreen, some of the flavor components are volatilized, but sufficient flavor remains to give a product having a strong, high impact flavor. Fruit flavors, that may contain esters, are more easily volatilized and may be flammable and/or explosive and therefore, generally these type of fruit flavors may be pretreated in order to be able to add them to a gum coating.

In an embodiment of this invention, a lipophilic active agent is preblended with a gum arabic solution to become a paste and then applied to the cores. To reduce stickiness, the preblend may be mixed with a small amount of coating syrup before being applied. Forced air drying is then continued as the gum arabic binds the active agent to the cores. Then additional coatings are applied to cover the active agent and imbed the active agent in the coatings.

Gum Formulation Examples

The following examples of the invention and comparative examples are provided by way of explanation and illustration.

As noted earlier, the gum formulas can be prepared as sugar or sugarless type formulations. These formulas are made in a pellet or pillow shape pellet or a round ball or any other shape of product for coating/panning. However, gum formulas for pellet centers are generally adjusted to a higher level of gum base than stick gum to give a more consumer acceptable size of gum bolus.

Keeping this in mind, if a coating of about 25% of the total product is added to a pellet core as sugar or polyols, the gum base in the pellet core should also be increased by 25%. Likewise, if a 33% coating is applied, the base levels should also be increased by 33%. As a result, gum centers are usually formulated with about 25% to about 40% gum base with a corresponding decrease in the other ingredients except flavor. Even higher levels of base may be used when an active agent is added to a pellet coating. Generally flavors increase with the level of gum base as the base tends to bind flavors into the gum and more flavor is needed to give a good flavorful product. However flavors can also be added to the coating to give increased flavor impact and more flavor perception.

EXAMPLES

Conventional coated gum compositions may contain a lipophilic active agent in the gum coating. When this composition is chewed for 30 minutes about 50% of the lipophilic active releases from the chewed gum as determined by gum bolus analysis. It was believed that the lipophilic active agent was being bound into the lipophilic gum base composition and not being released. As a result, tests were made comparing conventional gum bases and their release of a lipophilic active agent from conventional non-coated gum formulations.

The following tests of gum bases were made with the following gum formula:

|  | % |
|---|---|
| Base | 19.65 |
| Sugar | 53.68 |
| 39 DE, 43 Be syrup | 13.33 |
| Dextrose, Monohydrate | 9.90 |
| Glycerin | 1.29 |
| Peppermint flavor | 0.90 |
| Lecithin | 0.25 |
| Vitamin E acetate | 1.00 |
|  | 100.00 |

Several conventional and non-conventional bases formulations were first tested.

|  | Comparative Example A | Comparative Example B* | Comparative Example C |
|---|---|---|---|
| Glycerol Ester of Hyd. Rosin | 20.4% | — | — |
| Butyl Rubber | — | 2.0% | — |
| Terpene Resins | — | — | 25.9% |
| Isobutylene/isoprene/copolymer | — | — | 10.3% |
| High MW PVAc | 36.9% | 31.5% | — |
| Low MW PVAc | — | 43.75% | 27.3% |
| Polyisobutylene | 11.9% | 6.0% | 2.3% |
| Glycerol Triacetate | 5.7% | 6.75% | — |
| Glycerol Monostearate | 4.5% | — | 4.7% |
| Acetylated Monoglycerides | 3.9% | — | — |
| Hydrogenated Vegetable Oil | — | — | 3.2% |
| Wax | — | — | 12.4% |
| Lecithin | — | — | 1.4% |
| Talc | 16.7% | — | — |
| Color | — | — | 0.6% |
| Calcium Carbonate | — | 10.0% | 11.9% |
|  | 100.0% | 100.0% | 100.0% |
| Vitamin E released** | 0.21% | 2.88% | 0.52% |

*Example 1 base formulation from U.S. Pat. No. 5,601,858.
**Vitamin E acetate released from gum bolus after 30 minutes chewing.

In order to increase the release of vitamin E acetate from the gum bolus during chewing, the following hydrophilic gum bases were made:

|  | Example 1 % | Example 2 % | Example 3 % | Example 4 % |
|---|---|---|---|---|
| High MW PVAc | 31.000 | 28.630 | 27.600 | 27.280 |
| Low MW PVAc | 43.00 | 39.795 | 38.400 | 37.840 |
| Oat Fiber | 12.00 | 11.100 | 10.000 | 22.560 |
| Glycerol Triacetate | 7.000 | 6.475 | 10.000 | 6.160 |
| MCTs*** | 7.000 | 14.000 | 14.000 | 6.160 |
|  | 100 | 100 | 100 | 100 |
| Vitamin E released** | 34.2 | 59.0 | 57.0 | 43.1 |

***Medium chain triglycerides

Chewing gum formulations were made from these base compositions using the gum formula noted previously and the gum bolus was analyzed for vitamin E acetate after 30 minutes of chewing. These results, which show the amount of vitamin E acetate released, indicate that the hydrophilic base compositions above gave an improved release of vitamin E acetate, a lipophilic active agent. A hydrophilic base should release at least 10% of a lipophilic active agent, and more preferably at least 30% within 30 minutes of chewing. If this type of base can be used to give an improved release from the gum, then using it as part of a gum core and adding the lipophilic active agent to the gum coating, the release should be even greater still.

The following gum base and gum formula was made into pellets for coating:

| Example 5 Base Formula % | |
|---|---|
| High MW PVAc | 26.35 |
| Low MW PVAc | 36.65 |
| Calcium Carbonate | 10.00 |
| Glycerol Triacetate | 13.00 |
| MCTs | 14.00 |
|  | 100.00 |

| Example 5 Gum Formula % | |
|---|---|
| Base | 33.00 |
| Calcium Carbonate | 13.00 |
| Sorbitol Powder | 39.70 |
| Glycerin | 12.00 |
| Peppermint Flavor | 0.96 |
| Encapsulated Sweeteners | 1.34 |
|  | 100.00 |

These centers were then precoated with a mannitol Quick Coat material from Wolf & Olsen. Precoat was done by making a 40% solution of Quick Coat and applying to the gum centers to wet the centers and then applying a dry charge of the powder Quick Coat material. This was done twice as a precoat. Then a hard shell coating of xylitol with Vitamin E acetate was applied to 1 Kg of centers to the following formula:

| Example 5 Coating Formula, grams | | |
|---|---|---|
|  | Syrup 1 | Syrup 2 |
| Xylitol | 509 | 509 |
| Water | 90 | 90 |
| 40% Gum Talha Solution | 168.5 | 168.5 |
| Titanium Dioxide | 3 | 3 |
| Peppermint Flavor* | 4 | — |
| Vitamin E Acetate** | 16 | — |

*Flavor added with two applications (about 10th and 20th coat)
**Liquid vitamin E acetate added in 4 application between flavor applications.

The gum center weight was 1.25 grams per piece and was coated to a 1.91 grams per piece weight to give a 34.5% coating. Although nearly all of the acetate is released in 10 minutes, coated gum product was chewed for 30 minutes and the gum bolus was analyzed for vitamin E acetate and gave an 80.8% release. This is much higher than previous amounts of lipophilic actives being released from conventional coated gum formulations.

It should be appreciated that the compositions and methods of the present invention are capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention, therefore, indicated by the appended claims rather than by the foregoing description. All changes which come within the meaning and range of equivalency of the claims are to be embraced within their scope.

What is claimed is:

1. A hydrophilic chewing gum base comprising:
   a) about 20% to about 90% hydrophilic polymers;
   b) about 5% to about 35% hydrophilic softeners/emulsifiers; and
   c) about 4% to about 50% filler;
   d) the chewing gum base being essentially free of hydrophobic polymers, elastomer solvents, waxes and hydrophobic softeners.

2. The hydrophilic gum base of claim 1 wherein the hydrophilic polymers are selected from the group consisting of polyvinyl acetate, short and medium chain polyesters, short and medium chain polyamides, and short and medium side chain polyvinyl esters and combinations thereof.

3. The hydrophilic gum base of claim 1 wherein the hydrophilic polymers are selected from the group consisting of high molecular weight is polyvinyl acetate, low molecular weight polyvinyl acetate, polyvinyl butyrates, polyvinyl propionates and combinations thereof.

4. The hydrophilic gum base of claim 1 wherein the hydrophilic softeners/emulsifiers are selected from the group consisting of glycerol monostearate, glycerol triacetate, lecithin, mono-, and diglycerides, short and medium chain triglycerides, acetylated monoglycerides, and combinations thereof.

5. The hydrophilic gum base of claim 1 wherein the filler is selected from the group consisting of magnesium carbonate, calcium carbonate, ground limestone, magnesium silicate, aluminum silicate, clay, alumina, talc, titanium oxide, mono-, di- and tri-calcium phosphate, cellulose polymers and combinations thereof.

6. The hydrophilic gum base of claim 1 wherein the base is free of butyl elastomers, polyisobutylene and styrene butadiene rubber.

7. The hydrophilic gum base of claim 1 wherein the base is free of of terpene resins, rosin esters and ester gums.

8. The hydrophilic gum base of claim 1 wherein the gum base, when admixed into a non-coated chewing gum product, the gum product including lipophilic active agents, releases at least 10% of the lipophilic active agent from the chewing gum product within 30 minutes of chewing.

9. A chewing gum product made using the gum base of any one of claims 1–8.

10. A coated chewing gum product comprising:
    a) a chewing gum core made from a hydrophilic gum base, the gum base being essentially free of hydrophobic polymers, elastomer solvents, waxes and hydrophobic softeners; and
    b) a coating on the core, the coating including a lipophilic active agent.

11. The coated chewing gum product of claim 10 wherein the lipophilic active agent is selected from the group consisting of vitamins, cancer chemotherapeutics, antimycotics, oral contraceptives, analgesics, antacids, muscle relaxants, antihistamines, decongestants, anesthetics, antitussives, diuretics, anti-inflammatories, antibiotics, antivirals, psychotherapeutic agents, anti-diabetic agents, cardiovascular agents, bioengineered pharmaceuticals, nutraceuticals and nutritional supplements.

12. A method of producing coated chewing gum products containing at least one lipophilic active agent in the coating comprising the steps of:
    a) providing chewing gum product cores wherein the chewing gum is made from a hydrophilic gum base, the gum base being essentially free of hydrophobic polymers, elastomer solvents, waxes and hydrophobic softeners;
    b) providing a coating solution;
    c) coating the chewing gum product cores with the coating solution to provide coated chewing gum products, the coating including a lipophilic active agent at a level of from about 12 micrograms to about 250 milligrams per gram of coated chewing gum product.

13. The method of claim 12 wherein the active agent is mixed in the coating solution prior to coating the cores.

14. The method of claim 13 wherein the active agent is also mixed with a solvent before adding to the coating solution and the resulting mixture is added to the chewing gum coating.

15. The method of claim 14 wherein the solvent is water, alcohol or flavor.

16. The method in claim 12 wherein a high-potency sweetener selected from the group consisting of aspartame, alitame, salts of acesulfame, cyclamate and its salts, saccharine and its salts, neotame, thaumatin, monellin, dihydrochalcones, sucralose and combinations thereof is mixed in the coating solution.

17. The method of claim 12 wherein said lipophilic active agent is selected from the group consisting of vitamins, analgesics, antacids, antihistamines, antitussives, antibacterial agents, decongestants and anesthetics.

18. The method of claim 12 wherein the active agent is a nutraceutical.

19. The method of claim 12 wherein said active agent is vitamin E.

20. The method of claim 12 wherein the coating operation includes the application of multiple coats of coating solution and application of powder material between coats of coating solution.

21. The method of claim 20 wherein the active agent is included in the powder material.

22. The method of claim 20 wherein active agent is included in both the coating solution and the powder material.

23. The method of claim 12 wherein a lipophilic active agent is also included in the chewing gum cores.

24. The method of claim 23 wherein the active agents in the gum cores and coating are the same.

25. The method of claim 23 wherein the active agent in the cores is different than the active agent in the coating.

26. The method of claim 12 wherein at least two different coating solutions are used to make the coating.

27. The method of claim 26 wherein the active agent is mixed with the first of the at least two different coating solutions and applied to form a film, and a second coating solution without an active agent is applied over the film coated cores.

28. The method of claim 12 wherein the active agent is present in the coating at a level of from about 10 ppm to about 30% of the coating.

29. A method of delivering a lipophilic active agent comprising the steps of:
    a) providing a chewing gum product having i) a chewing gum core made using a hydrophilic gum base, the gum base being essentially free of hydrophobic polymers, elastomer solvents, waxes and hydrophobic softeners, and ii) a coating including a lipophilic active agent in the coating; and b) chewing the chewing gum product for at least 10 minutes in an oral cavity of an individual chewing the chewing gum product.

30. The method of claim 29 wherein the active agent is chosen from the group consisting of: vitamins; analgesics; muscle relaxants; antibiotics; antivirals; antihistamines; decongestants; anti-inflammatories; antacids; psychotherapeutic agents; and cardiovascular agents.

* * * * *

UNITED STATES PATENT AND TRADEMARK OFFICE
CERTIFICATE OF CORRECTION

PATENT NO.    : 6,350,480 B1  
DATED         : February 26, 2002  
INVENTOR(S)   : Philip W. Urnezis et al.

It is certified that error appears in the above-identified patent and that said Letters Patent is hereby corrected as shown below:

Title page, Item [54] and Column 1, lines 1-3,  
Delete "CHEWING GUM PRODUCT INCLUDING A HYDROPHILIC GUM BASE AND METHOD OF PRODUCING" and substitute -- RELEASE OF LIPOPHILIC ACTIVE AGENTS FROM CHEWING GUM -- in its place.

Column 13,  
Line 16, delete extra space before "about".

Signed and Sealed this

Second Day of December, 2003

JAMES E. ROGAN  
*Director of the United States Patent and Trademark Office*